(12) United States Patent
Hanna et al.

(10) Patent No.: US 6,998,125 B2
(45) Date of Patent: Feb. 14, 2006

(54) SYNERGISTIC COMPOSITION AND METHODS FOR TREATING NEOPLASTIC OR CANCEROUS GROWTHS AND FOR RESTORING OR BOOSTING HEMATOPOIESIS

(75) Inventors: Nabil Hanna, Olivenhain, CA (US); Gary R. Braslawsky, San Diego, CA (US); Kandasamy Hariharan, San Diego, CA (US)

(73) Assignee: Biogen IDEC Inc., Cambridge, MA (US)

( * ) Notice: Subject to any disclaimer, the term of this patent is extended or adjusted under 35 U.S.C. 154(b) by 0 days.

(21) Appl. No.: 09/853,581

(22) Filed: May 14, 2001

(65) Prior Publication Data

US 2001/0019715 A1    Sep. 6, 2001

Related U.S. Application Data

(62) Division of application No. 08/933,359, filed on Sep. 18, 1997, now abandoned.

(51) Int. Cl.
  *A61K 39/385*   (2006.01)
  *A61K 39/395*   (2006.01)
(52) U.S. Cl. .............................. 424/193.1; 424/195.11; 424/178.1; 424/182.1
(58) Field of Classification Search ............. 424/184.1, 424/193.1–203.1, 277.1, 178.1, 182.1
  See application file for complete search history.

(56) References Cited

U.S. PATENT DOCUMENTS

| | | | |
|---|---|---|---|
| 5,514,670 A | 5/1996 | Friedman et al. | 514/2 |
| 5,585,103 A | 12/1996 | Raychaudhuri et al. | 424/278.1 |
| 5,695,770 A * | 12/1997 | Raychaudhuri et al. | 424/278.1 |
| 5,709,860 A | 1/1998 | Raychaudhuri et al. | |
| 5,932,212 A | 8/1999 | Khalaf | |
| 6,197,311 B1 | 3/2001 | Raychaudhuri et al. | |
| 2002/0004052 A1 * | 1/2002 | Berd et al. | 424/277.1 |

FOREIGN PATENT DOCUMENTS

WO   WO94/09815    5/1994
WO   WO 9409815 A1 *  5/1994

OTHER PUBLICATIONS

Wojtowicz-Praga et al. (Jnl. Immunology. May 1996, vol. 19. No. 3, pp. 169-175).*
Arteaga et al. (J.Clin.Invest., Dec. 1993, vol. 92, pp. 2569-2576).*
Hoefer et al. (Cancer Immunol. Immunother, 1995, vol. 41, pp. 302-308).*
Matar et al. (Eur. J. Cancer, May 2000, vol. 36 No. 8, pp. 1060-1066).*
Berd et al. (Cancer Research, vol. 46, May 1986, pp. 2572-2577).*
Jianyin, L et al., May 1997, "Clinical Applications and Prospects of the Transforming Growth Factor B" Junshi Yixue Kexueyuan Yuankan Huagong, vol. 21, No. 2, pp. 135-139 (translated by FLS, Inc.).*
Dybedal et al., "Transforming Growth Factor $\beta$ (TGF-$\beta$), A Potent Inhibitor of Erythropoiesis: Neutralizing TGF-$\beta$ Antibodies Show Erythropoietin as a Potent Stimulator of Murine Burst-Forming Unti Erythroid Colony Formation in the Absence of a Burst-Promoting Activity", Blood, 86(3): 949-957 (1995).
Sitnicka et al., "Transforming Growth Factor $\beta_1$ Directly and Reversibly Inhibits the Initial Cell Divisions of Long-Term Repopulating Hematopoietic Stem Cells", Blood, 88(1):82-88 (1996).
Jacobsen et al., "Transforming Growth Factor-$\beta$ Potently Inhibits the Viability-Promoting Activity of Stem Cell Factor and Other Cytokines and Induces Apoptosis of Primitive Murine Hematopoietic Progenitor Cells", Blood, 86(8): 2957-2966 (1995).
Clarke et al., "Lisofylline Inhibits Transforming Growth Factor $\beta$ Release and Enhances Trilineage Hematopoietic Recovery after 5-Fluorouracil Treatment in Mice", Cancer Research, 56:105-112 (1996).
Kopp et al., "Transforming Growth Factor $\beta 2$ (TGF-$\beta 2$) Levels in Plasma of Patients with Metastatic Breat Cancer Treated with Tamoxifen[1]", Cancer Research, 55:4512-4515 (1995).
Sansilvestri et al., "Early CD34$^{high}$ Cells Can Be Separated Into KIT$^{high}$ Cells in Which Transforming Growth Factor-$\beta$ (TGF-$\beta$) Downmodulates c-*kit* and KIT$^{low}$ Cells in Which Anti-TFG-$\beta$ Upmodulates c-*kit*", Blood, 86(5):1729-1735 (1995).
Jianyin, L et al., "Clinical application and potential of TGF$\beta$," Beijing Institute of Basic Medical Sciences, May 1997, pp. 135-140.
Hallinan et al., "Aminoacetyl moiety as a potential surrogate for diacylhydrazine group of SC-51089, a potent PGE2 antagonist, and its analogs," J Med Chem., 1996, 39:609-613.
Oka et al., "PGE2 receptor subtype EP1 antagonist may inhibit central interleukin-1$\beta$-induced fever in rats,"The American Physiological Society, 1998, R1762-1765.

(Continued)

Primary Examiner—Gary B. Nickol
(74) Attorney, Agent, or Firm—Pillsbury Winthrop Shaw Pittman LLP

(57) ABSTRACT

The present invention provides a synergistic composition and methods for treating neoplastic or cancerous growths as well as for treating such patients in order to restore or boost hematopoiesis. The present invention comprises administration of the combination of a cytotoxic T-lymphocyte inducing composition and at least one agent which is capable of neutralizing or down regulating the activity of tumor secreted immunosuppressive factors, separately or in combination.

19 Claims, 6 Drawing Sheets

OTHER PUBLICATIONS

Isaac et al., "Successful treatment of established rat prostate cancer by transforming growth factor-B1 antisense transfected tumor vaccine," *J of Urology,* 197, 157:270.

Murphy et al., "Differential effects of growth hormone and prolactin on murine T cell development and function," *J Exp Med.,* 1993, 178:231-6.

Richards et al., "Prolactin is an antagonist of TGF-beta activity and promotes proliferation of murine B cell hybridomas," *Cell Immunol.,* 1998, 184:85-91.

Francis R. Carbone and Michael J. Bevan, "Class I-Restricted Processing and Presentation of Exogenous Cell-Associated with Antigen In Vivo," Feb. 1990, 171:377-387.

Hidemi Takahashi, Toshiyuki Takeshita, Bror Morein, Scott Putney, Ronald N. Germain and Jay A. Berzofsky, "Induction of CD8+ Cytotoxic T Cells by Immunization with Purified HIV-1 Envelope Protein in ISCOMs" *Nature,* Apr. 26, 1990, 344:873-875.

Mark W. Moore, Francis R. Carbone, and Michael J. Bevan, "Introduction of Soluble Protein into the Class I Pathway of Antigen Processing and Presentation" *Cell,* Sep. 9, 1988, 54:777-785.

Brown et al., Either interleukin-12 or interferon-gamma can correct the dendritic cell defect induced by transforming growth factor beta in patients with myeloma. Br J Haematol. Jun 2004;125(6):743-8. Abstract only.

Comerci et al., Altered expression of transforming growth factor-beta 1 in cervical neoplasia as an early biomarker in carcinogenesis of the uterine cervix. Cancer. Mar 15, 1996; 77(6):1107-14. Abstract only.

De Wever et al.,Critical role of N-cadherin in myofibroblast invasion and migration in vitro stimulated by colon-cancer-cell-derived TGF-{beta} or wounding. J Cell Sci. Oct 15, 2004;117(Pt 20):4691-4703. Epub Aug. 25, 2004. Abstract only.

Hasegawa et al., Transforming growth factor-beta1 level correlates with angiogenesis, tumor progression, and prognosis in patients with nonsmall cell lung carcinoma. Cancer. Mar 1, 2001;91(5):964-71. Abstract only.

Lee et al., Aberrant expression of Smad4 results in resistance against the growth-inhibitory effect of transforming growth factor-beta in the SiHa human cervical carcinoma cell line. Int J Cancer. Nov 15, 2001;94(4):500-7. Abstact.

Matsunaga et al., Splenic marginal zone lymphoma presenting as myelofibrosis associated with bone marrow involvement of lymphoma cells which secrete a large amount of TGF-beta. Ann Hematol. May 2004;83(5):322-5. Epub Nov 11, 2003. Abstractonly.

Medrano et al., Repression of TGF-beta signaling by the oncogenic protein SKI in human melanomas: consequences for proliferation, survival, and metastasis. Oncogene. May 19, 2003;22(20):3123-9. Abstract only.

Mitani, Molecurlar mechanisms of leukemogenesis by AML1/EVI-1. Oncogene. May 24, 2004;23(24):4263-9. Abstract only.

Mitropoulos et al., Expression of transforming growth factor beta in renal cell carcinoma and matched no-involved renal tissue. Urol Res. Sep 7, 2004 [Epub ahead of print]. Abstract only.

Matar et al., Down regulation of T-cell-derived IL-10 production by low-dose cyclophosphamide treatment in tumor-bearing rats restores in vitro normal lymphoproliferative response. Int Immunopharmacol. Feb 2001;1(2):307-19. Abstract only.

Piestrzeniewicz-Ulanska et al., Expression and intracellular localization of Smad proteins in human endometrial cancer. Oncol Rep. Sep-Oct 2003;10(5):1539-44. Abstract only.

Sacco et al., Transforming growth factor beta1 and soluble Fas serum levels in hepatocellular carcinoma. Cytokine. Jun 2000;12(6):811-4. Abstract only.

Schiemann et al. Transforming growth factor-beta (TGF-beta)-resistant B cells from chronic lymphocytic leukemia patients contain recurrent mutations in the signal sequence of the type I TGF-beta receptor. Cancer Detect Prev. 2004; 28(1):57-64. Abstract only.

Seoane et al., Integration of Smad and forkhead pathways in the control of neuroepithelial and glioblastoma cell proliferation. Cell. Apr 16, 2004;117(2):211-23. Abstract only.

Shariat et al., Preoperative plasma levels of transforming growth factor beta(1) (TGF-beta(1)) strongly predict progression in patients undergoing radical prostatectomy. J Clin Oncol. Jun 1, 2001;19(11):2856-64. Abstract only.

Shariat et al., Preoperative plasma levels of transforming growth factor beta(1) strongly predict clinical outcome in patients with bladder carcinoma. Cancer. Dec 15, 2001;92 (12):2985-92. Abstract only.

Sheen-Chen et al., Serum levels of transforming growth factor beta1 in patients with breast cancer. Arch Surg. Aug 2001;136(8):937-40. Abstract.

Subramanian et al. Targeting endogenous transforming growth factor beta receptor signaling in SMAD4-deficient human pancreatic carcinoma cells inhibits their invasive phenotype1. Cancer Res. Aug 1, 2004;64(15):5200-11. Abstract only.

Lian et al., Enhanced expression of transforming growth factor-beta isoforms in the neural tube of embryos derived from diabetic mice exposed to cyclophosphamide. Neurosci Lett. Nov 6, 2003;351(1):51-5. Abstract.

Weiner et al., Treatment of multiple sclerosis with cyclophosphamide: critical review of clinical and immunologic effects. Mult Scler. Apr 2002;8(2):142-54. Abstract only.

Xu et al., Elevated serum levels of transforming growth factor beta1 in Epstein-Barr virus-associated nasopharyngeal carcinoma patients. Int J Cancer. Aug 20, 1999;84(4):396-9. Abstract only.

Xi et al., Dysregulation of the TGF-beta postreceptor signaling pathway in cell lines derived from primary or metastatic ovarian cancer. J Huazhong Univ Sci Technolog Med Sci. 2004;24(1):62-5. Abstract only.

Xiong et al., Transforming growth factor-beta1 in invasion and metastasis in colorectal cancer. World J Gastroenterol. Aug 2002;8(4):674-8. Abstract.

Takiguchi et al., Profile of cytokines produced in tumor tissue after administration of cyclophosphamide in a combination therapy with tumor necrosis factor. Anticancer Res. 2004, 24(3a):1823-8. Abstract only.

Crispens et al., "Evaluation of the anticancer activities of Tweens 20, 40 and 60 in SJL/J mice," Anticancer Res., 1991, 11(1):407-8 (abstract only).

Miller et al., "The Purification and Characterization of the Cytochrome d Terminal Oxidase Complex of the Escherichia coll Aerobic Respiratiry Chain," J Biol. Chem., 1983, 258(15):9159-9165 (only p. 9159 is attached).

Blondino et al., "The quantitative determination of aspirin and its degradation products in a model solution aerosol," J Pharm Biomed Anal., 1995, 13(2):111-9 (abstract only).

Morris et al., "Structural properties of polyethylene glycol-polysorbate 80 mixture, a solid dispersion vehicle," 1992, J Pharm Sci. 81(12):1185-8 (abstract only).

Schmolka, "A Review of Block Copolymer Surfactants," J. Am. Oil. Chem. Soc., 1977, 54(3):110-116 (copy attached).

Hunter et al., "The Adjuvant Activity of Nonionic Block Polymer Surfactants," J. Immunol., 1981, 127(3):1244-1249 (copy attached).

* cited by examiner

SYNERGISTIC COMPOSITION AND METHODS FOR TREATING NEOPLASTIC OR CANCEROUS GROWTHS AND FOR RESTORING OR BOOSTING HEMATOPOIESIS

CROSS REFERENCE TO RELATED APPLICATION

This application is a divisional of U.S. Ser. No. 08/933,359, filed Sep. 18, 1997, now abandoned, the content of which is incorporated herein by reference in its entirety.

BACKGROUND OF THE INVENTION

1. Field of the Invention

This invention relates to a composition and method for treating humans and animals for neoplastic or cancerous growths as well as treating such patients in order to restore or boost hematopoiesis. The composition of the present invention comprises a combination of a cytotoxic T-lymphocyte inducing composition and an agent which is capable of neutralizing or down regulating the activity of tumor secreted immunosuppressive factors.

2. Description of the Related Art

Cytotoxic T-lymphocytes (CTLs) are believed to be the major host mechanism in response to a variety of viral infections and neoplastic or cancerous growth (Greenberg et al., *Adv. Immunol.*, 49:281–355 (1991); Baxevanis et al., *Crit. Rev. Oncol.-Hematol.*, 16:157–79 (1994); Ward et al., *Biological Approaches to Cancer Treatment, Biomodulation*, pp. 72–97, edited by M. S. Mitchel, New York: McGraw Hill, Inc. (1993)). These cells eliminate infected or transformed cells by recognizing antigen fragments in association with various molecules (termed class I MHC molecules) on the infected or transformed cells (Baxevanis et al., *Crit. Rev. Oncol.-Hematol.*, 16:157–79 (1994); Matsumura et al., *Science*, 257:927–34 (1992); Long et al., *Immunol. Today*, 10:232–34 (1989)).

The use of soluble forms of tumor associated antigens (TAA) in subunit vaccines to stimulate tumor specific T-cell immunity is a desirable strategy for developing a safe and effective immunotherapy for cancers. The advantage of using whole protein is that after antigen processing in specialized antigen presenting cells (APC) it contains the entire repertoire of potential peptide epitopes. However, the immunization with whole soluble antigen generally does not activate CTLs. Therefore, to stimulate CTL response to specific protein antigens, various approaches focusing on improving the intracellular antigen delivery to APC have been tried. These include live viral (Moss, B., *Science*, 252: 1662–67 (1991); Takahashi et al., *PNAS USA*, 85:3105–09 (1988)) and bacterial (Aldovini et al., *Nature (London)*, 351:479–482 (1991); Sadoff et al., *Science*, 240:336–38 (1988)) vectors, non-replicating plasmid DNA inoculation (Ulmer et al., *Science*, 259:1745–49 (1993)), conjugation of protein and peptides to lipophilic compounds (Deres et al., *Nature (London)*, 342:561–64 (1989)) or ISCOM (Takahashi et al., *Nature (London)*, 344:873–75 (1990)). The major concerns for vaccines, based on viral vectors or DNA injections, are safety relating to possible DNA integration into the host cell genome which is particularly relevant to oncogenes with transforming potentials and the induction of anti-vector response in vivo. Furthermore, in immunocompromised individuals, it is safer to use purified antigens in combination with an appropriate non-infectious delivery system with minimal toxicity to induce an immune response.

A safe and advantageous composition by which CTL response may be induced in humans and domesticated or agriculturally important animals and includes the whole soluble protein in a non-infectious delivery system was discovered by Raychaudhuri et al. (U.S. Pat. No. 5,585,103), the contents of which are hereby incorporated by reference in its entirety. The CTL inducing composition involves the use of an antigen formulation which has little or no toxicity to animals, and lacks an immunostimulating peptide (e.g., muramyl dipeptide), the presence of which would decrease the desired response. More specifically, the CTL inducing composition (PROVAX™) comprises the antigen to which the CTL response is desired and a non-toxic antigen formulation which comprises, consists or consists essentially of a stabilizing detergent, a micelle-forming agent, and a biodegradable and biocompatible oil.

However, it has been documented that tumors escape from immune surveillance by secreting factors or cytokines that exert immunosuppressive effects on the functions of both activated and precursor immune cells present locally and systemically. Therefore, cancer patients receiving therapeutic vaccines alone, vaccines which are aimed at enhancing the tumor immunity, may not fully benefit from such vaccine.

Additionally, cancer patients, especially at late stages of the disease, show suppressed hematopoietic activity due to suppression of stem and/or progenitor cells that are vital for the maintenance of healthy bone marrow. This suppression is a result of compounding factors, including radiation and chemotherapy which is used in cancer treatment as well as immunosuppressive factors that may be upregulated by cancer treatments, such as, for example, transforming growth factor-β (TGFβ), a stable family of polypeptide growth factors which are secreted by normal as well as the growing tumors of the host.

Therefore, in view of the aforementioned deficiencies attendant with previously known cancer vaccines and methods of treating tumors, it should be apparent that there still exists a need in the art for more efficient immunotherapeutic treatments and compositions.

SUMMARY OF THE INVENTION

The inventors of the present application have surprisingly discovered that the therapeutic efficacy of a vaccine which is aimed at enhancing tumor immunity, by induction of a CTL response can be increased when such CTL inducing vaccine is used in conjunction with one or more agents which are capable of neutralizing, antagonizing, down regulating or blocking tumor-secreted immunosuppressive factors, e.g., TGFβ and IL-10.

Accordingly, an object of the present invention is to provide a composition comprising any adjuvant formulation capable of inducing CTL in combination with one or more agents which are capable of neutralizing, blocking, antagonizing or down regulating the activity of tumor secreted factors. A particular preferred CTL inducing adjuvant comprises the CTL inducing adjuvants disclosed in U.S. Pat. No. 5,585,103, issued to Raychaudhuri et al., which comprise the following: an antigen to which an antigen-specific CTL response is to be induced agonist and a microfluidized antigen formulation, said antigen formulation comprising:

(i) a stabilizing detergent,
(ii) a micelle-forming agent, and
(iii) a biodegradable and biocompatible oil, and further wherein said antigen formulation lacks an immunostimulating peptide component and is formulated as a stable oil-in-water emulsion. Preferably the agent(s) which are capable of neutralizing, blocking, antagonizing or down regulating tumor-secreted immunosuppressive factors will include anti-TGFβ antibodies, transforming growth factor-β receptor fusion proteins (TGFβR-fusion proteins), TGFβ antagonists such as thrombospondin peptides, TGFβ binding proteins and TGFβR blocking antibodies.

Another object of the present invention is to provide a method of treatment which includes the induction of a CTL response wherein the improvement comprises the use of an adjuvant which induces a CTL response and an antagonist of an immunosuppressive factor, preferably TGFβ, said adjuvant and antagonist can be administered sequentially or concurrently in either order.

A further object of the invention is to provide a method of treating neoplastic or cancerous growths in a patient in need of such treatment.

An additional object of the present invention is to provide a method of restoring or boosting hematopoiesis in a patient.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

Figure 1:
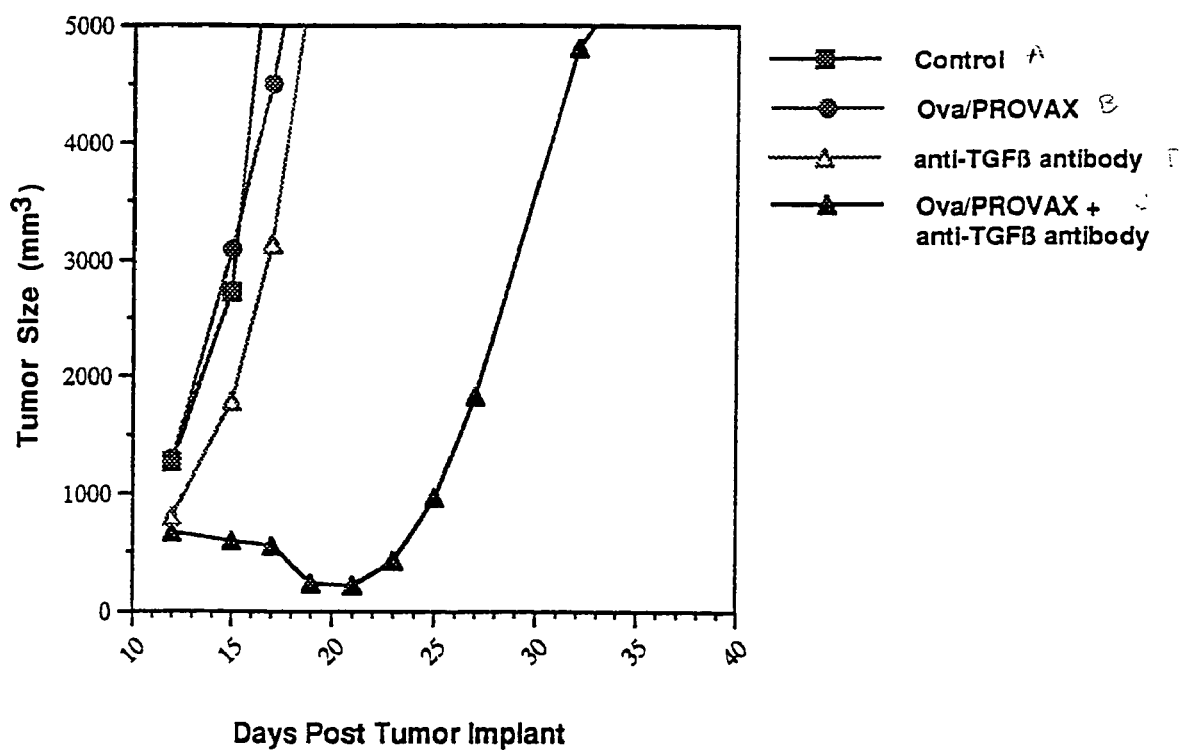
FIG. 1 represents the antitumor activity of ovalalbumin/PROVAX™ and/or anti-TGFβ antibody treatment on established EG7 tumors.

As discussed supra, the inventors of the present application have unexpectedly discovered that the therapeutic efficacy of a vaccine which is aimed at enhancing tumor immunity, e.g., a CTL inducing adjuvant, is increased when it is used in conjunction with one or more agents which are capable of neutralizing or down regulating tumor secreted immunosuppressive factors. The inventors have surprisingly discovered that this combination results in synergistic enhancement of cytotoxic T lymphocyte response, thereby resulting in enhanced therapeutic response against targeted antigen-expressing cells, e.g., a tumor. Additionally, the inventors have discovered that the use of one or more agents which neutralize or down regulate the tumor secreted immunosuppressive factors in combination with the vaccine or adjuvant assists in restoring or boosting hematopoiesis.

The soluble inhibitory or immunosuppressive factors or cytokines which are secreted by tumor cells in order to avoid immune destruction include, for example, transforming growth factor β (TGFβ) (Mukherj et al., Curr. Opin. Oncol., 7:175 (1995)), interleukin 10 (IL 10) (Huber et al., J. Immunol., 148:277 (1992)), prostaglandin (PGF2) (Huang et al., J. Immunol., 157:5512–20 (1996)), immunosuppressive acidic protein (IAP) (Yamaguchi et al., Oncology, 52:1–6 (1995)) and Lipocortin-1 (LC1) (Koseki et al., Surg. Today, 27:30–39 (1997)). TGFβ has been shown as a tumor associated immunosuppressive molecule from studies done in the glioblastoma (Brooks et al., J. Exp. Medicine, 136: 1631–47 (1972)). Ample evidence indicates that TGFβ is produced by a variety of human cancer cells, including breast carcinoma (Knabbe et al., Cell, 48:417–28 (1987)), prostatic carcinoma (Ikeda et al., Biochemistry, 16:2406–10 (1987)), colorectal carcinoma (Coffey et al., Cancer Res., 46:1164–69 (1986)), endometrial carcinoma (Boyd et al., Cancer Res., 50:3394–99 (1990)) and ovarian carcinoma (Wilson et al., P. R. Br. J. Cancer, 63:102–08 (1991)).

TGFβ was originally identified by its ability to impart a transformed phenotype to normal fibroblasts and found to be produced by virtually all the cells (Wakefield et al., J. Cell. Biol., 105:965–75 (1987)). In humans, it is found in three different isoforms, TGFβ 1, 2 and 3. TGFβ is a pleiotropic cytokine which affects a wide range of biological activities, including immunosuppression, inflammation, hematopoiesis and wound repair (Sporn et al., Science, 233:532 (1986); Pallidino et al., Ann. NY Acad. Sci., 593:181 (1990); Roberts et al., Adv. Cancer Res., 51:107 (1988).

Of particular relevance is the potent immunosuppressive activity of TGFβ (Pallidino et al., Ann. NY Acad. Sci., 593:181 (1990); Roberts et al., Adv. Cancer Res., 51:107 (1988); Lucas et al., J. Immunol., 145:1415–22 (1990)). TFGβ could exert immunosuppression by inhibiting, T and B cell proliferation (Kehrl et al., J. Exp. Med., 163:1037 (1986); Kehrl et al., J. Immunol., 137:3855 (1986); Kehrl et al., J. Immunol., 143:1868 (1989)), LAK cell/CTL generation (Mulé et al., Cancer Immunol. Immunother., 26:9 (1988); Espevik et al., J. Immunol., 140:2312 (1988); Rook et al., J. Immunol, 136:3916 (1986); Ranges et al., J. Exp. Med., 166:991 (1987); Fontana et al., J. Immunol., 143:323 (1989); Susan et al., J. Exp. Med., 172:1777 (1990); Torre-Amione et al., PNAS, 87:1486 (1990) and function, NK cell activity (Rook et al.,J. Immunol., 136:3916 (1987); Susan et al., J. Exp. Med., 172:1777 (1990); Torre-Amione et al., PNAS, 87:1486 (1990)) macrophage oxygen metabolisms (Tsunawaki et al., Nature, 334:260 (1988)), IgG and IgM secretion (Kehrl et al., J. Immunol., 137:3855 (1986); Kehri et al., J. Immunol., 143:1868 (1989) or by down regulating the Human Leukocyte Antigen (HLA-DR) (Czarniecki et al., J. Immunol., 140:4217 (1988); Zuber et al.,Eur. J. Immunol., 18:1623 (1988) and IL-2R (Kehrl et al., J. Exp. Med., 163:1037 (1986)).

Also of particular relevance is the affect TGFβ has on hematopoiesis. TGFβ has been shown to negatively regulate and even inhibit the growth of primitive hematopoietic cells (Sitnicka et al., Blood, 88(1):82–88 (1996); Dybedal et al., Blood, 86(3):949–57 (1995)). Antagonist of TGFβ could, therefore, play an important role in improving established cancer therapies that are characterized by having dose-limiting myeloid suppression. Suppression is a result of compounding factors which may include both direct effects of the cancer therapeutics on hematopoiesis and indirect effects by upregulation of immunosuppressive factor. For example, Barcellos-Hoff et al., J. Clin. Invest., 93:892–99 (1994) demonstrated that ionizing radiation of mice leads to a rapid increase in levels of active TGFβ in mammary tissue and concomitant loss of latent TGFβ.

The active form of TGFβ is a 25 kD homodimeric protein that is synthesized and secreted as a latent precursor form which becomes active presumably upon enzymatic cleavage (Massague et al., *Ann. Rev. Cell. Biol.,* 6:597–641 (1990)) although the exact method(s) of activation in vivo have not as yet been elucidated. There is 70% similarity found within each of the 3 major isoforms, TGFβ 1, 2 and 3. Presumably, the actions of activated TGFβ are mediated via binding to various cell surface receptors. At least 3 different TGFβ receptors, TGFβR-1, TGFβR-2 and TGFβR-3 have been identified (Barnard et al., *Biochim. Biophys. Acta,* 1032: 79–87 (1990)). All three receptors are type I integral membrane glycoproteins and ubiquitously expressed by virtually all cells in the body, except TGFβR-3 which is absent in monocytes. Both TGFβ and its receptors have been cloned and expressed. Other TGFβ membrane binding components have been described on fully differentiated subsets of cells and are not ubiquitously expressed. In particular endoglin (CD105), primarily expressed on endothelial and pre-B cells, has recently been shown to bind TGFβ-1 and β3 isoforms (Zhang et al., *J. Immunol.,* 156:565–573 (1996))

There have been various attempts to neutralize and/or down regulate the activity of TGFβ. For example, antibodies which are specific for TGFβ have been suggested for use in treating tumor cells that produce TGFβ to counteract the immunosuppressive effects of TGFβ (Segarini et al., WO 94/09815). TGFβ-specific antibodies have also been found to restore or boost the growth of primitive hematopoietic cells, such as progenitor and stem cells, which were suppressed due to excess TGFβ production (Dybedal et al., *Blood,* 86(3):949–57 (1995); Sitnicka et al., *Blood,* 88(1): 82–88 (1996)).

A number of other strategies may be used to neutralize or down regulate the active form of TGFβ. For example, TGFβ receptor (TGFβR) Fc-fusion proteins, especially the receptor II fusion proteins may be administered to neutralize or down regulate TGFβ in vivo. Antibodies to TGFβ receptor may block the interaction of free TGFβ to the TGFβR and prevent downward signaling events in the target cell. Also, analogs of TGFβ or TGFβ binding proteins, e.g., thrombospondin peptides, could compete with free TGFβ for the binding to the receptor and inactivate the receptor. Further, gene therapy approaches may be utilized in order to achieve the above. Additional strategies have been described to prevent activation of TGFβ from its latent form which does not participate in signaling events. For example, thrombospondin peptide sequences have been described and synthesized which inhibit activation of latent TGFβ (Schultz-Cherry et al., *J. Biol. Chem.,* 270:7304–7310 (1995)).

At least one agent capable of neutralizing or down regulating the biological activity of tumor or host secreted immunosuppressive factors is present in a therapeutically effective amount. In a preferred embodiment the agent is present in an amount ranging from about 5 to about 1000 mg per square meter.

The CTL inducing composition involves the use of an antigen formulation which has little or no toxicity to animals, and lacks an immunostimulating peptide (e.g., muramyl dipeptide), the presence of which would decrease the desired response. More specifically, the CTL inducing composition comprises the antigen to which the CTL response is desired and a non-toxic antigen formulation which comprises, consists or consists essentially of a stabilizing detergent, a micelle-forming agent, and a biodegradable and biocompatible oil. This antigen formulation preferably lacks any immunostimulating peptide component, or has sufficiently low levels of such a component that the desired cellular response is not diminished. This formulation is preferably provided as a stable microfluidized oil-in-water emulsion. That is, each of the various components are chosen such that the emulsion will remain in an emulsion state for a period of at least one month, and preferably for more than one year, without phase separation. The antigen and antigen formulation are mixed together to form a mixture, and that mixture can be administered to the animal in an amount sufficient to induce CTL response in the animal.

By "non-toxic" is meant that little or no side effect of the antigen formulation is observed in the treated animal or human. Those of ordinary skill in the medical or veterinary arts will recognize that this term has a broad meaning. For example, in a substantially healthy animal or human only slight toxicity may be tolerated, whereas in a human suffering from terminal disease (with a life expectancy of less than about three years) substantially more toxicity may be tolerated.

By "stabilizing detergent" is meant a detergent that allows the components of the emulsion to remain as a stable emulsion. Such detergents include polysorbate 80 (TWEEN 80) (Sorbitan-mono-9-octadecenoate-poly(oxy)-1,2-ethanediyl; manufactured by ICI Americas, Wilmington, Del.), TWEEN 40 (polyoxyethylenesorbitan monopalmitate), TWEEN 20 (polyoxyethylenesorbitan monolaurate), TWEEN 60, (polyoxyethylenesorbitan monostearate), ZWITTERGENT 3-12, (N-dodecyl-N,N-dimethyl-3-ammonio-1-propanesulfonate), TEEPOL HB7 (alkyl (C9–C13) sodium sulfates), and SPAN 85 sorbitan trioleate). These detergents are usually provided in an amount of approximately 0.05 to 0.5%, preferably at about 0.2%.

By "micelle-forming agent" is meant an agent which is able to stabilize the emulsion formed with the other components such that a micelle-like structure is formed. Such agents preferably cause some irritation at the site of injection in order to recruit macrophages to enhance the cellular response. Examples of such agents include PEG1000 (polyethylene glycol having average molecular weight of 1000), and block polymer surfactants such as those described by BASF Wyandotte publications, e.g., Schmolka, *J. Am. Oil. Chem. Soc.,* 54:110 (1977) and Hunter et al., *J. Immunol.,* 127(3):1244 (1981), both hereby incorporated by reference. Such surfactants are called block polymers because they contain polyoxypropylene (POP) and polyoxyethylene (POE) portions which occur in separate blocks, and include PLURONIC L62LF, L101, and L64, L121 (poloxamer 401), and TETRONIC 1501, 150R1, 701, 901, 1301, and 130R1. The chemical structures of such agents are well known in the art. For example, PLURONIC L121 (poloxamer 401) has the general structure: $(POE)_a$-$(POP)_b$-$(POE)_a$, as shown below:

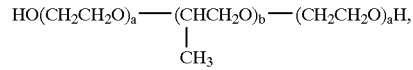

wherein a and b are such that the average molecular weight of the polyoxypropylene blocks in the molecule is 4000, and approximately 10% of the molecular weight of the copolymer is composed of the polyoxyethylene blocks. Preferably, the agent is chosen to have a hydrophile-lipophile balance (HLB) of between 0 and 2, as defined by Hunter and Bennett, *Journal of Immunology,* 133:3167 (1984). The agent is preferably provided in an amount between 0.001 and 10%, most preferably in an amount between 0.001 and 5%.

The oil is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE, tetratetracontane, glycerol, and peanut oil or other vegetable oils. The oil is preferably provided in an amount between 1 and 10%, most preferably between 2.5 and 5%. It is important that the oil is biodegradable and biocompatible so that the body can break down the oil over time, and so that no adverse affects, such as granulomas, are evident upon use of the oil.

It is important in the above formulation that a peptide component, especially a muramyl dipeptide (MDP) be lacking. Such a peptide will interfere with induction of a CTL response if it provided in an amount greater than about 20 micrograms per normal human formulation administration. It is preferred that such peptides are completely absent from the antigen formulation, despite their apparent stimulation of the humoral compartment of the immune system. That is, although such peptides may enhance the humoral response, they are disadvantageous when a cytotoxic T-lymphocyte response is desired.

The antigen formulation can be formed from only two of the above three components and used with any desired antigen (which term includes proteins, polypeptides, and fragments thereof which are immunogenic), to induce a CTL response in the above animals or humans.

In preferred embodiments, the method consists essentially of a single administration of the mixture (antigen plus antigen formulation) to the human or the animal; the human or animal is infected with a cancer or virus and suffers one or more symptoms (as generally defined by medical doctors in the relevant field) of infection from the cancer or virus; and the antigen formulation is non-toxic to the human or animal.

In other preferred embodiments, the antigen is chosen from melanocytic differentiation antigens, for example: gp100 (Kawakami et al., *J. Immunol.* 154:3961–3968 (1995); Cox et al., *Science,* 264:716–719 (1994)), MART-1/Melan A (Kawakami et al., *J. Exp. Med.,* 180:347–352 (1994); Castelli et al., *J. Exp. Med.,* 181:363–368 (1995)), gp75 (TRP-1) (Wang et al., *J. Exp. Med.,* 186:1131–1140 (1996)), and Tyrosinase (Wolfel et al., *Eur. J. Immunol.,* 24:759–764 (1994); Topalian et al., *J. Exp. Med.,* 183: 1965–1971 (1996)); melanoma proteoglycan (Hellstrom et al., *J. Immunol.,* 130:1467–1472 (1983); Ross et al., *Arch. Biochem Biophys.,* 225:370–383 (1983)); tumor-specific, widely shared antigens, for example: antigens of MAGE family, for example, MAGE-1, 2, 3, 4, 6, and 12 (Van der Bruggen et al., *Science,* 254:1643–1647 (1991); Rogner et al., *Genomics,* 29:729–731 (1995)), antigens of BAGE family (Boel et al., *Immunity,* 2:167–175 (1995)), antigens of GAGE family, for example, GAGE-1,2 (Van den Eynde et al., *J. Exp. Med.,* 182:689–698 (1995)), antigens of RAGE family, for example, RAGE-1 (Gaugler et al., *Immunogenetics,* 44:323–330 (1996)), N-acetylglucosaminyltransferase-V (Guilloux et al., *J. Exp. Med.,* 183:1173–1183 (1996)), and p15 (Robbins et al., *J. Immunol.,* 154:5944–5950 (1995)); tumor specific mutated antigens; mutated β-catenin (Robbins et al., *J. Exp. Med.,* 183:1185–1192 (1996)), mutated MUM-1 (Coulie et al., *Proc. Natl. Acad. Sci. USA,* 92:7976–7980 (1995)), and mutated cyclin dependent kinases-4 (CDK4) (Wolfel et al., *Science,* 269:1281–1284 (1995)); mutated oncogene products: p21 ras (Fossum et al., *Int. J. Cancer,* 56:40–45 (1994)), BCR-abl (Bocchia et al., *Blood,* 85:2680–2684 (1995)), p53 (Theobald et al., *Proc. Natl. Acad. Sci. USA,* 92:11993–11997 (1995)), and p185 HER2/neu (Fisk et al.,*J. Exp. Med.,* 181:2109–2117 (1995)); Peoples et al., *Proc. Natl. Acad. Sci., USA,* 92:432–436 (1995)); mutated epidermal growth factor receptor (EGFR) (Fujimoto et al., *Eur. J. Gynecol. Oncol.,* 16:40–47 (1995)); Harris et al., *Breast Cancer Res. Treat,* 29:1–2 (1994)); carcinoembryonic antigens (CEA) (Kwong et al.,*J. Natl. Cancer Inst.,* 85:982–990 (1995)); carcinoma associated mutated mucins, for example, MUC-1 gene products (Jerome et al., *J. Immunol,* 151: 1654–1662 (1993), Ioannides et al., *J. Immunol.,* 151:3693–3703 (1993), Takahashi et al., *J. Immunol.,* 153: 2102–2109 (1994)); EBNA gene products of EBV, for example, EBNA-1 gene product (Rickinson et al., *Cancer Surveys,* 13:53–80 (1992)); E7, E6 proteins of human papillomavirus (Ressing et al., *J. Immunol.,* 154:5934–5943 (1995)); prostate specific antigens (PSA) (Xue et al., *The Prostate,* 30:73–78 (1997)); prostate specific membrane antigen (PSMA) (Israeli, et al., *Cancer Res.,* 54:1807–1811 (1994)); PCTA-1 (Sue et al., *Proc. Natl. Acad. Sci. USA,* 93:7252–7257 (1996)); idiotypic epitopes or antigens, for example, immunoglobulin idiotypes or T cell receptor idiotypes, (Chen et al., *J. Immunol.,* 153:4775–4787 (1994); Syrengelas et al., *Nat. Med.,* 2:1038–1040 (1996)); antigens of HIV: gp160, gag, pol, nef, Tat and Rev; the malaria antigens: CS protein and Sporozoite surface protein 2; the Hepatitis B surface antigens: Pre-S1, Pre-S2, HBc Ag, and HBe Ag; the influenza viral antigens: HA, NP and NA; Hepatitis A surface antigens; Hepatitis C surface antigens; the Herpes virus antigens: HSV gB, HSV gD, HSV gH, HSV early protein product, human papillomavirus antigens, cytomegalovirus gB, cytomegalovirus gH and IE protein gp72; respiratory syncytial virus antigens: F protein, G protein and N protein.

The CTL inducing adjuvant can be combined with the agent which is capable of neutralizing, blocking, antagonizing or down regulating the activity of tumor secreted immunosuppressive factors and administered to the patient as a single composition or the two components can be administered separately. Administration can be achieved via numerous well known techniques. Such modes of administration include, for example, intradermal injection, subcutaneous injection, intraperitoneal injection, and intramuscular injection. Furthermore, administration of agents capable of neutralizing or down regulating immunosuppressive molecules can be administered separately independent of adjuvant administration, for example intravenously or intraperitoneally. The preferred embodiment is to administer the antigen containing CTL inducing adjuvant formulation intradermally, intramuscularly or subcutaneously and the neutralizing agent systemically via intravenous administration.

Synergism should be observed in any disease condition where immunosuppressive factors such as TGFβ have an adverse effect on the host's ability in being able to elicit a therapeutic CTL response. Such diseases include by way of example many cancers and neoplastic growths, viral infections and parasitic infections. Cancers which can be treated using the subject synergistic combination include, by way of example, breast cancer, brain cancer, cervical cancer, leukemia, lymphoma, prostate cancer, skin cancer, colon cancer, lung cancer, ovarian cancer, pancreatic cancer, liver cancer, bladder cancer, kidney cancer, myeloma, colorectal cancer, nasoparingeal carcinoma and endometrial cancer. Viral and parasitic infections treatable according the invention include, for example, papillomavirus, malaria, Hepatitis, Herpes, cytomegalovirus, respiratory syncytial virus and HIV. As discussed above, another important aspect of the invention includes the induction of hematopoiesis. This is of significant therapeutic importance in, for example, cancer therapies.

In this regard, it is well known that cancer patients, especially at late stages of the disease, show suppressed hematopoietic activity due to suppression of stem or progenitor cells. This suppression is a result of factors such as radiation and chemotherapy which is used in cancer treatment as well as immunosuppressive factors which are secreted by tumors. Treatment with the inventive combination composition allows hematopoiesis to be restored or boosted. Moreover, it should further improve chemo or radio therapy as it should enable the therapeutic dosages to be administered without adverse effects.

The following examples are presented in order to more fully illustrate the preferred embodiments of the invention. They should in no way be construed, however, as limiting the broad scope of the invention.

EXAMPLES

Example 1

Mice were inoculated with ovalbumin expressing EG7 cells ($2 \times 10^6$ cells/mouse). Derivation of EG7 is described previously by Moore et al., Cell, 54:777 (1988). On day 7, post-inoculation mice bearing 250–350 mm³ size tumors were sorted in to 5 groups and treated as follows: Group A, the control group received no antigen injection (■), Group B received 30 µg of ovalbumin in PROVAX s.c. (●), Group C received 30 µg ovalbumin in PROVAX™ s.c. and 50 µg of anti-TGFβ antibodies i.p. per mouse (▲), and Group D received 50 µg of anti-TGFβ antibodies i.p. (Δ). The data as set forth in FIG. 1 indicates that the treatment of mice bearing progressively growing EG7 tumors with anti-TGFβ antibodies in conjunction with ovalbumin in PROVAX™ gave enhanced anti-tumor activity under conditions where treatment with ovalbumin-PROVAX™ is not effective.

Example 2

Mice were inoculated with HPV-E7 expressing HOPE2 cells ($4 \times 10^6$ cells mouse) (2.A.). E7 expressing HOPE2 transfectant was obtained by electroporation of an E7 encoding mammalian expression plasmid into K1735-X21 cells (Kind gift from Dr. Isaiah J. Fidler). The Human Papillomavirus Type 16 E7 expression vector, INPEP4+LE7, contains a 300 bp E7 encoding fragment (amino acid residues 2–97; Seedorf et al., Virology, 145:181–185 (1985)) fused downstream of an immuglobulin leader sequence (L). Transcription is driven by the Cytomegalovirus promoter/enhancer (CMV) and the bovine growth hormone (BGH) 3' flanking sequence provides a polyadenylation signal for RNA processing. Bacterial neomycin phosphotransferase (N) and mammalian dihydrofolate reductase (DHFR) expression cassettes, driven by the mouse beta-globin major promoter (BETA), allow dominant selection by G418 and methotrexate, respectively. The neomycin gene cassette includes the SV40 early polyadenylation signal (SV40) for RNA processing. Plasmid DNA is linearized by restriction digestion with PAC I prior to electroporation. K1735-X21 cells were grown in MEM Alpha medium (Gibco BRL.) supplemented to 10% (v/v) non-essential amino acids (Irvine Sci.), 10% (v/v) L-glutamine (Irvine Sci.), 20% (v/v) MEM Vitamin solution (Gibco BRL.), 1 mM Sodium Pyruvate (Biowhittaker), and 5% FBS (Gibco BRL.). 1 µg of Pac I linearized INPEP4+LE7 DNA was electroporated into $4 \times 10^6$ K1735-X21 cells and using a BTX 600 Electroporator (375 volts, 13 ohms, and 25 microfaradays). The cells were plated in a 96 well flat bottom plate. After 24 hours of incubation, the cells were fed by media supplemented with 0.4 mg/ml active G418. G418 resistant clones were screened for E7 expression by ELISA, Western and Northern blot analyses and selected for further expansion. HOPE2 was positive for E7 expression by all of the above analyses.

Figure 2A:
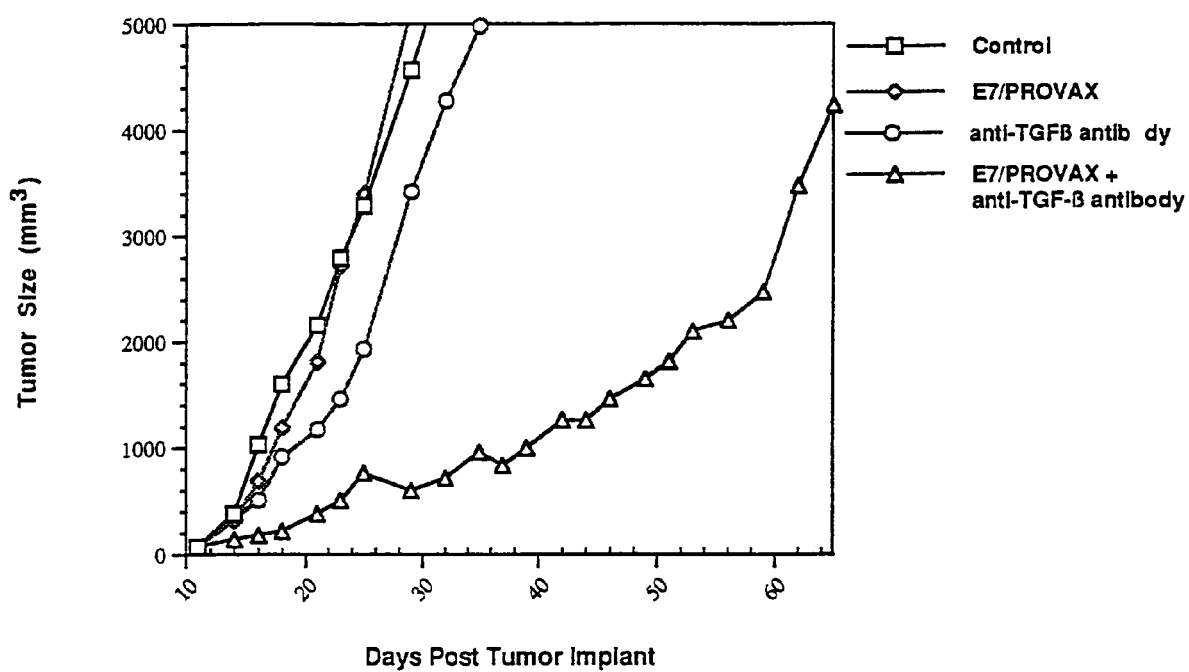
FIGS. 2A and 2B represent the antitumor activity of E7/PROVAX™ and/or anti-TGFβ antibody treatment on HOPE2 cells.

On day 11 post-inoculation, mice bearing 75–150 mm³ size tumors were sorted in to 4 groups and treated as follows: Group A, the control group received no antigen injection (□), Group B received 30 µg of E7 in PROVAX™ s.c. (◇), Group C received 30 µg ovalbumin in PROVAX™ s.c. and 100 µg of anti-TGFβ antibodies i.p. per mouse (Δ) and Group D received single i.p. injection of 100 µg of anti-TGFβ antibodies (○). The data as set forth in FIG. 2A indicates that the treatment of mice bearing progressively growing HOPE2 tumors with anti-TGFβ antibodies in conjunction with E7-PROVAX™ gave enhanced anti-tumor activity.

Figure 2B:
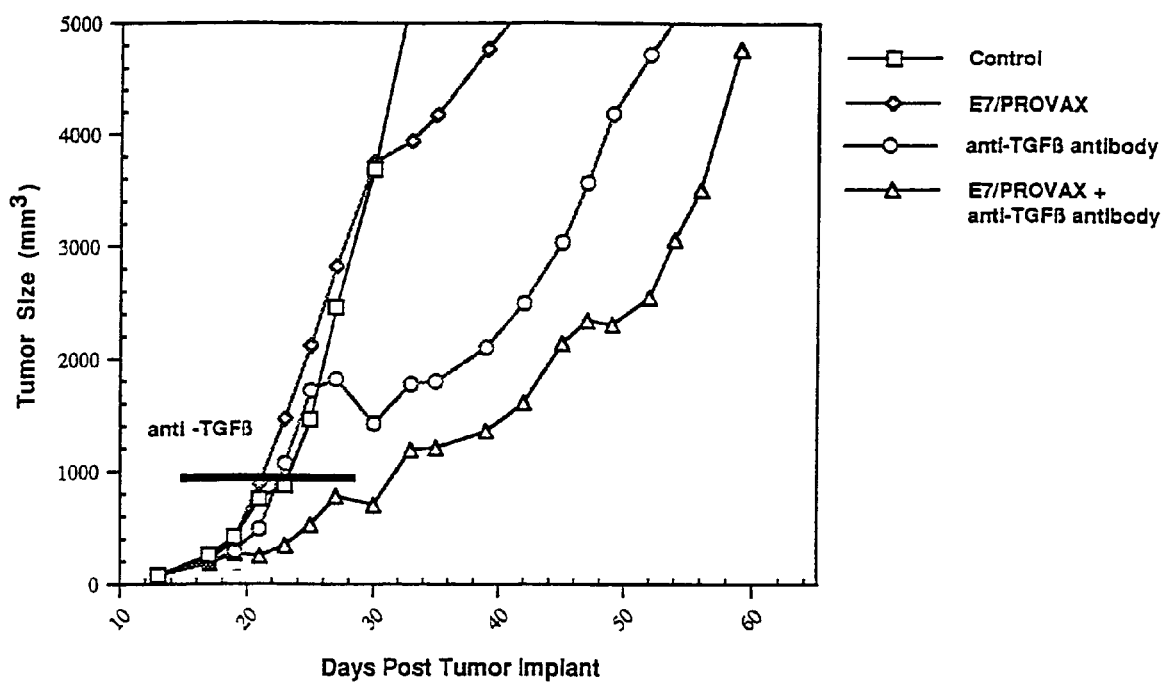

In another experiment, on day 13 post HOPE2 inoculation, mice were sorted and grouped as above. These groups of mice were treated similar to 2.A., except for Group C(Δ) and D(○), which received 4 injections of anti-TGFβ antibodies every 4 days between day 15–29 (2.B.). The results are set forth in FIG. 2B.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art. Furthermore, all of the publications, patents and patent applications cited herein are incorporated by reference in their entirety.

Example 3

Figure 3A:
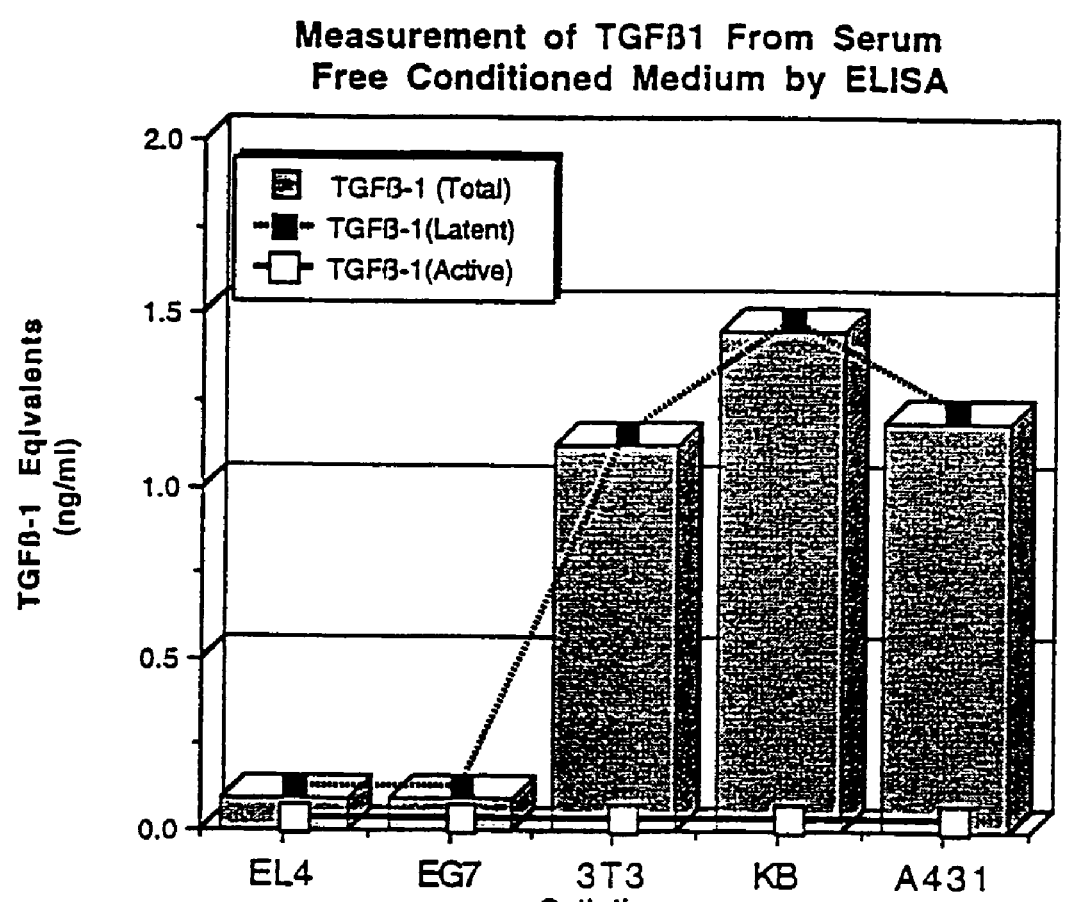
FIGS. 3A and 3B represent the estimated level of the activated or latent forms of TGFβ-1 secreted by various cell lines after in vitro incubation in serum free medium (CHO-S SFM II, GIBCO, Cat. #91-0456) for 2 days (EL4; EG7 cells) or 5 days (3T3, KB and A431 cells) continuous culture at 37° C.
Figure 3B:
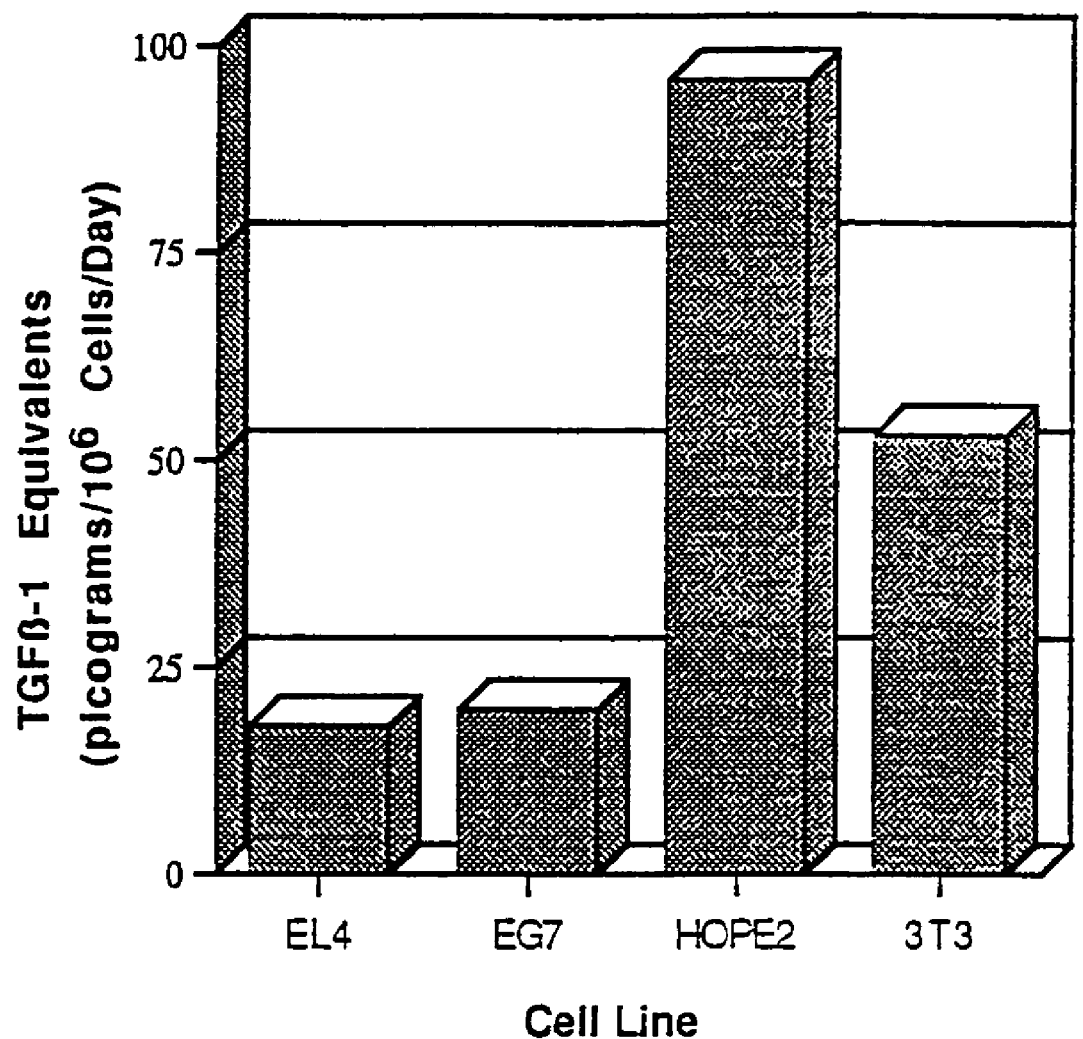

The concentration of TGFβ1 secreted by murine cell lines 3T3 (BALB/c origin), HOPE2 (C3H origin) EL4, and EG7 (C57BL/6) and human cell lines KB (epidermoid carcinoma ATCC #CCL-17) and A431 (epidermoid carcinoma, ATCC #CRL-1555) were measured by TGFβ1 ELISA kit (Genzyme Corp., Cat. #80-3108). FIGS. 3A and 3B measure the TGFβ1 concentration from serum free conditioned medium (CM) using GIBCO CHO-S SFM II (Cat. #91-0456) after either 3 days (Cell Lines EL4 and EG7) or 5 days (KB, A431 and HOPE2) of continuous culture in vitro at 37° C. CM was centrifuged at 400×g for 5 minutes before analyzing for TGFβ concentration as per manufactures instructions FIG. 3A measures the activity of CM directly (fully active TGFβ1) and after acid activation followed by neutralization according to manufacturers instructions (total TGFβ1). The fraction of latent TGFβ1 in CM was estimated by subtracting the active concentration of TGFβ from the total TGFβ concentration. As shown in FIG. 3A all cell lines incubated in vitro secreted TGFβ1, and ≧98% of the secreted material was in the latent form.

FIG. 3B estimates the level of TGFβ1 in conditioned medium from the various cell lines after normalization for the total cell number present after the 2 or 5 days incubation at 37° C.

Example 4

Figure 4:
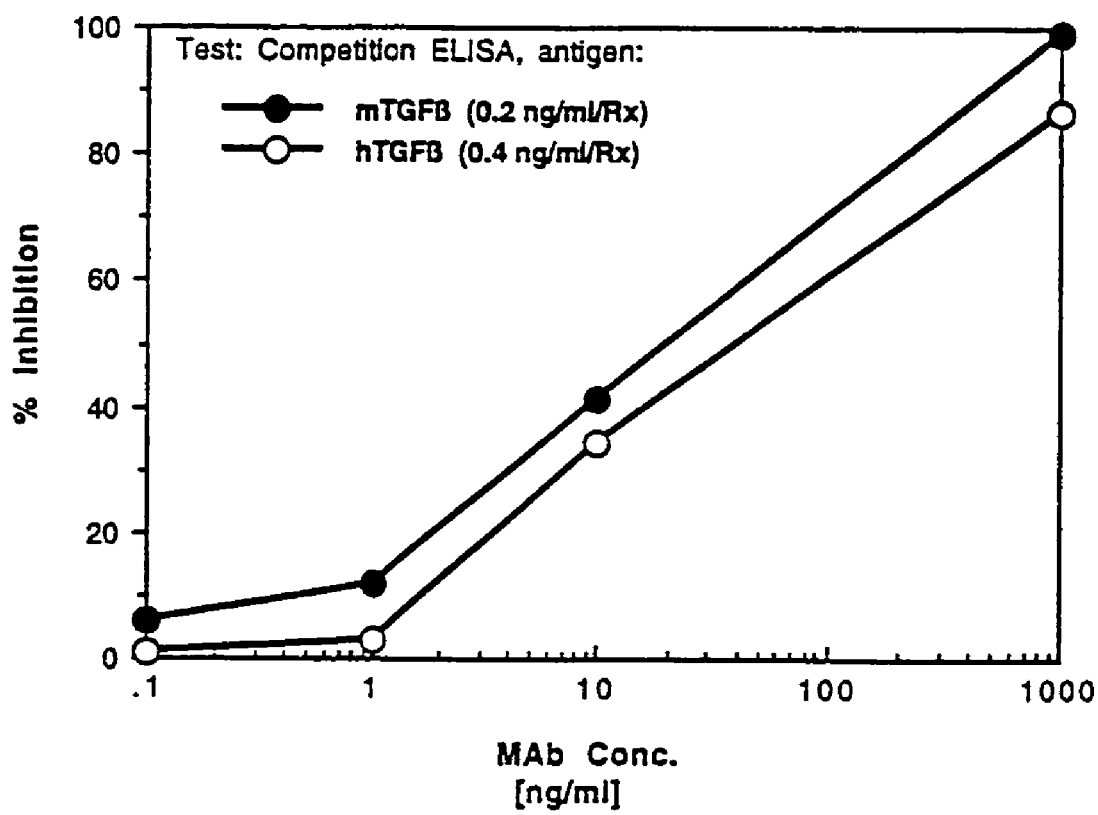
FIG. 4 represents binding of monoclonal mouse anti-TGF-β1, β2, β3 (Genzyme Corp: Cat. #80-1835-03) for mouse or human TGFβ present in conditioned medium obtained from either human A431 cells or murine BALB/c 3t3 cells.

FIG. 4 demonstrates the binding activity of the anti-TGFβ neutralizing antibody for either murine or human TFGβ, after acid activation and neutralization according to manufactures instructions. Murine TGFβ was obtained from BALB/c 3T3 conditioned medium (see FIG. 3) and diluted with PBS to 0.2 ng/ml, and human TGFβ was obtained from A431 CM and diluted with PBS to 0.4 ng/ml. Conditioned medium was incubated with various dilutions of monoclonal mouse anti-TGF-β1, β2, β3 (Genzyme Corp: Cat. #80-1835-03) for 3 hours at 4° C. and assayed for unconjugated TGFβ using the ELISA assay described in FIG. 3. The anti-TGFβ neutralizing antibody shows comparable binding to TGFβ from both human and murine sources.

What is claimed is:

1. A method of treating cancer comprising administering to a patient in need thereof:
    (a) an admixture comprising a cancer or tumor antigen expressed by cells of the cancer to be treated and a microfluidized antigen formulation comprising:
        (i) a stabilizing detergent,
        (ii) a micelle-forming agent, and
        (iii) a biodegradable and biocompatible oil,
said antigen formulation being formulated as a stable oil-in-water emulsion;
    wherein said admixture is administered to said patient in an amount sufficient to induce a cytotoxic T-lymphocyte response in said patient which is specific for the cancer or tumor antigen contained in said admixture, and
    (b) a therapeutically effective amount of at least one agent which is capable of neutralizing, blocking, antagonizing, or down regulating the activity or preventing activation of transforming growth factor β (TGFβ) specifically, which agent is selected from the group consisting of an anti-TGFβ antibody, a TGFβR-fusion protein, a TGFβ analog, a TGFβ binding protein, and a TGFβR blocking antibody;
    wherein the antigen-containing admixture and the at least one agent which is capable of neutralizing, blocking, antagonizing, or down regulating the activity or preventing activation of TGFβ are administered sequentially or concurrently, and in any order.

2. The method of claim 1, wherein the antigen-containing admixture and the at least one agent which is capable of neutralizing, blocking, antagonizing, or down regulating the activity or preventing activation of TGFβ are administered sequentially.

3. The method of claim 1, wherein the antigen-containing admixture is administered intradermally, intramuscularly or subcutaneously and the at least one agent which is capable at neutralizing, blocking, antagonizing, or down regulating the activity or preventing activation of TGFβ is administered intravenously.

4. The method of claim 1, wherein the at least one agent which is capable of neutralizing, blocking, antagonizing, or down regulating the activity or preventing activation of TGFβ is a thrombospondin peptide or a TGFβR Fc-fusion protein.

5. The method of claim 1, wherein the admixture comprises a cancer or tumor antigen selected from the group consisting of gp100, MART-1/Melan A, gp75, tyrosinase, melanoma prateoglycan, MAGE, BAGE, GAGE, RAGE, N-acetylglucosaminyltransferase-V, mutated B-catenin, mutated MUM-1, mutated cyclin dependent kinases-4, p21 ras, BCR-abl, p53, p185 HER2/neu, mutated epidermal growth factor receptor, carcinoembryonic antigens, carcinoma associated mutated mucins, Epstein Barr nuclear antigen (EBNA) gene products, papillomavirus E7 protein, papillomavirus E6 protein, prostate specific antigens, prostate specific membrane antigen, and prostate carcinoma tumor antigen-1 (PCTA-1).

6. The method of claim 1, wherein the cancer is selected from the group consisting of breast cancer, brain cancer, cervical cancer, leukemia, lymphoma, prostate cancer, skin cancer, colon cancer, lung cancer, ovarian cancer, pancreatic cancer, liver cancer, bladder cancer, kidney cancer, myeloma, colorectal cancer, nasopharyngial carcinoma, or endometrial cancer.

7. The method of claim 1, wherein the detergent is provided in an amount ranging from approximately 0.05 to 0.5%.

8. The method of claim 7, wherein the amount of detergent is about 0.2%.

9. The method of claim 1, wherein the detergent is selected from the group consisting of sorbitan-mono-9-octadecenoate-poly(oxy)-1,2-ethanediyl, polyoxyethylene-sorbitan monolaurate, polyoxyethylenesorbitan monopalmitate, polyoxyethylenesorbitan monostearate, N-dodecyl-N, N-dimethyl-3-ammonio-1-propanesulfonate, alkyl ($C_9$–$C_{13}$) sodium sulfates, and sorbitan trioleate.

10. The method of claim 1, wherein the micelle-forming agent has a hydrophile-lipophile balance of between 0 and 2.

11. The method of claim 1, wherein the amount of the micelle-forming agent ranges from 0.5 to 10%.

12. The method of claim 11, wherein the amount of the micelle-forming agent ranges from 1.25 to 5%.

13. The method of claim 1, wherein the amount of oil ranges from 1 to 10%.

14. The method of claim 13, wherein the amount of oil ranges from 2.5 to 5%.

15. The method of claim 1, wherein the oil exhibits a melting temperature of less than 65° C.

16. The method of claim 1, wherein the oil is selected from the group consisting of squalane, eicosane, tetratetracontane, pristane, and vegetable oils.

17. The method of claim 1, wherein the antigen-containing admixture comprises sorbitan-mono-9-octadecenoate-poly(oxy)-1,2-ethanediyl, a block copolymer having the structure:

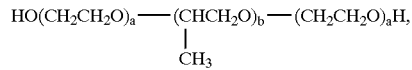

wherein a and b are such that the average molecular weight of the polyoxypropylene blocks in molecule is 4000 and approximately 10% of the molecular weight of the copolymer is composed of the polyoxyethylene blocks, and squalane.

18. The method of claim 1, wherein the antigen-containing admixture contains no more than 20 micrograms of an immunostimulating muramyl dipeptide.

19. The method of claim 1, wherein the antigen-containing admixture lacks an immunostimulating muramyl dipeptide.

* * * * *